United States Patent [19]
Maurer

[11] Patent Number: 5,092,320
[45] Date of Patent: Mar. 3, 1992

[54] KNEE BRACE WITH MAGNETIC SECURING MEANS

[75] Inventor: Donald D. Maurer, Anoka, Minn.

[73] Assignee: Empi, Inc., St. Paul, Minn.

[21] Appl. No.: 672,086

[22] Filed: Mar. 19, 1991

[51] Int. Cl.$^5$ .................................................. A61F 5/00
[52] U.S. Cl. ......................................... 602/26; 606/69; 606/72; 606/76
[58] Field of Search ............... 128/80 C, 80 F; 600/12; 623/20

[56] References Cited

U.S. PATENT DOCUMENTS

| | | | |
|---|---|---|---|
| 2,467,907 | 4/1949 | Peckham | 128/88 |
| 2,587,166 | 2/1952 | Jovick | 2/24 |
| 3,046,981 | 7/1962 | Biggs, Jr. et al. | 128/80 |
| 3,074,400 | 1/1963 | Schulman | 128/165 |
| 3,194,233 | 7/1965 | Peckham | 128/80 |
| 3,421,500 | 1/1969 | Jacobson | 272/67 |
| 3,581,741 | 6/1971 | Rosman | 128/80 |
| 3,587,572 | 6/1971 | Evans | 128/80 |
| 3,669,105 | 6/1972 | Castiglia | 128/80 C |
| 3,703,171 | 11/1972 | Schiavitto | 128/80 C |
| 3,786,804 | 1/1974 | Lewis | 128/80 C |
| 3,817,244 | 6/1974 | Taylor | 128/80 C |
| 4,024,588 | 5/1977 | Janssen et al. | 623/20 |
| 4,090,508 | 5/1978 | Gaylord, Jr. | 128/80 C |
| 4,275,716 | 6/1981 | Scott, Jr. | 128/80 C |
| 4,312,335 | 1/1982 | Daniell, Jr. | 128/80 C |
| 4,493,316 | 1/1985 | Reed et al. | 128/80 C |
| 4,503,846 | 3/1985 | Martin | 128/80 C |
| 4,628,916 | 12/1986 | Lerman et al. | 128/80 C |
| 4,726,362 | 2/1988 | Nelson | 128/80 C |
| 4,781,179 | 11/1988 | Colbert | 128/80 C |
| 4,791,916 | 12/1988 | Paez | 128/80 C |
| 4,793,333 | 12/1988 | Marquette | 128/80 C |

Primary Examiner—Richard J. Apley
Assistant Examiner—Susan L. Weinhoffer
Attorney, Agent, or Firm—Kinney & Lange

[57] ABSTRACT

A knee brace includes an upper support assembly pivotally attached to a lower support assembly. A magnetic assembly secures the upper and lower support assemblies to a leg of a wearer above and below the knee joint, respectively. The upper and lower support assemblies each include a pair of support elements engageable with the medial and lateral sides of a wearer's leg. A pair of polycentric hinge members pivotally connect the upper support elements to respective lower support elements. Flexible padded bands attached between the pairs of upper and lower support elements engage the thigh and calf of the leg. Stop members associated with the polycentric hinge members and support elements restrict extension of the wearer's leg. The magnetic assembly includes implanted magnets mounted directly to each of the medial and lateral sides of the femur and tibia beneath the tissue of the leg. Exterior magnets attached to the support elements cooperate with the implanted magnets to secure the knee brace to the leg of a wearer.

26 Claims, 2 Drawing Sheets

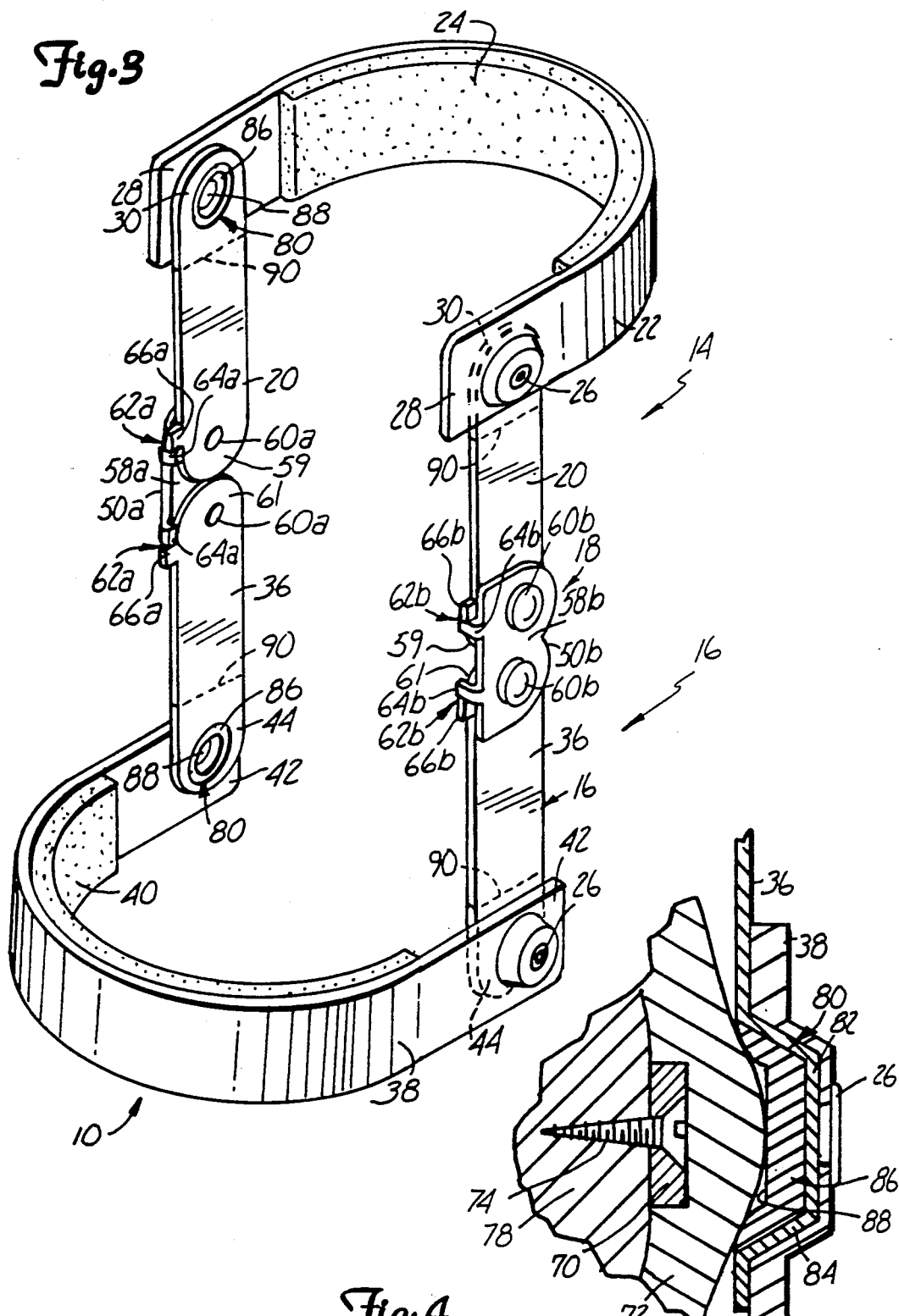

KNEE BRACE WITH MAGNETIC SECURING MEANS

BACKGROUND OF THE INVENTION

This invention pertains generally to an orthopedic brace and more particularly to a knee brace.

The human knee is the largest joint of the body, but due to its natural structure is the most vulnerable. The leg consists principally of a lower bone called the tibia and an upper bone known as the femur. The femur and tibia are hinged together at the knee joint. The knee joint includes femoral condyles supported in engagement with bearing like pads, called the medial and lateral menisci, positioned on the upper end of the tibia. The joint is held together by numerous ligaments, muscles and tendons, including the lateral ligaments and internal ligaments. The patella is a similarly supported bone positioned in front of the knee joint and acts as a shield for it. The joint is suspectable to damage if over extended or subjected to lateral or rotational trauma. Such trauma may result in anterior or posterior cruciate ligament injury or severance, medial/collateral ligament injury and/or medial/lateral menisci injuries. Damage to ligaments or other elements of the knee structure may cause the leg to become unstable and allow lateral wobble of the knee joint.

To promote healing, knee braces that prevent medial and lateral instability are used. Normally these braces: 1) provide derotation bracing to restrict rotation of the tibia relative to the femur about the knee joint; 2) prevent displacement of the tibia when the leg is flexed; and 3) protect collateral ligaments by using rigid vertical bracing elements on the medial and lateral sides of the knee joint.

U.S. Pat. No. 4,793,333 to Marquette discloses one such knee brace. The knee brace includes a tibial shell and a femoral shell joined together by a pair of joints. The femoral shell is configured to engage a posterior portion of the thigh and is secured to the leg of a wearer by a strap including hook and loop type fasteners. The tibial shell engages an anterior portion of the lower leg and is also secured by a strap including hook and loop fasteners. The joints are located to the medial and lateral sides of the knee joint. However, the objectives stated above are not well achieved since the bracing elements of the knee brace do not use the bones in the leg as a reference. The brace is attached to the flesh surrounding the knee joint and is therefore unstable relative to the leg bones.

It is evident that there is a continuing need for improved knee braces. Specifically, there is a need for a lightweight brace referenced mechanically to the tibia and femur that provides the stability necessary to mimic the support no longer provided by muscles in the injured knee.

SUMMARY OF THE INVENTION

The present invention is an orthopedic knee brace that, when secured to a wearer's leg, prevents medial and lateral instability of the knee joint. The brace includes an upper support assembly pivotally attached to a lower support assembly. A magnetic assembly secures the upper and lower support assemblies to the leg of a wearer above and below the knee joint, respectively.

The upper and lower support assemblies each include first and second support elements engageable with the medial and lateral sides of a wearer's leg. A pair of polycentric hinge members pivotally connect the upper support elements to respective lower support elements. A flexible band that includes a padded member is attached between the first and second upper support elements and engages a posterior portion of the thigh when the brace is secured to the wearer's leg. A similar flexible band is attached between the first and second lower support elements but engages the anterior portion of the wearer's calf.

Each polycentric hinge member includes a hinge plate having first and second pivot pins for pivotally connecting respective upper and lower support elements thereto. Each support element includes an L-shaped stop element that is engageable with a respective stop extension on the hinge plate. Engagement of the stop elements with the stop extensions upon rotation of the support elements relative to the hinge plate acts to restrict extension of the wearer's leg to 180° or less.

The magnetic assembly includes implanted magnets mounted directly to each of the medial and lateral sides of the femur and tibia beneath the tissue of the leg of a wearer. An exterior magnet is attached to each of the first and second support elements of the upper and lower support assemblies. All magnets are rare earth or cobalt magnets which are biocompatable with the human body. The polarity of the exterior magnets is opposite that of the implanted magnets and the strength of their mutual attraction acts to secure the brace to a leg of a wearer. Each exterior magnet includes a recess shaped to receive to a certain extent a respective implanted magnet to further help orient the brace in the proper position relative to the bones in the leg.

This knee brace is relatively uncomplicated and since it is referenced mechanically to the femur and tibia it provides enhanced medial and lateral stability to the knee joint. In addition, since the brace is referenced mechanically from the bones in the leg and not merely secured to the flesh surrounding the knee joint, it better mimics the support no longer provided by muscles and ligaments in the injured knee. Moreover, since this knee brace does not have large rigid, constricting cuffs with numerous straps, it provides better comfort and as a result causes fewer abrasions and pressure sores.

BRIEF DESCRIPTION OF THE DRAWINGS

FIG. 3 is a perspective view of the knee brace of the present invention.

FIG. 4 is an enlarged sectional view taken along the line 4—4 in FIG. 1 showing details of the magnetic assembly used to secure the knee brace to a leg of a wearer.

DETAILED DESCRIPTION OF THE PREFERRED EMBODIMENT

Figures 1, 2:
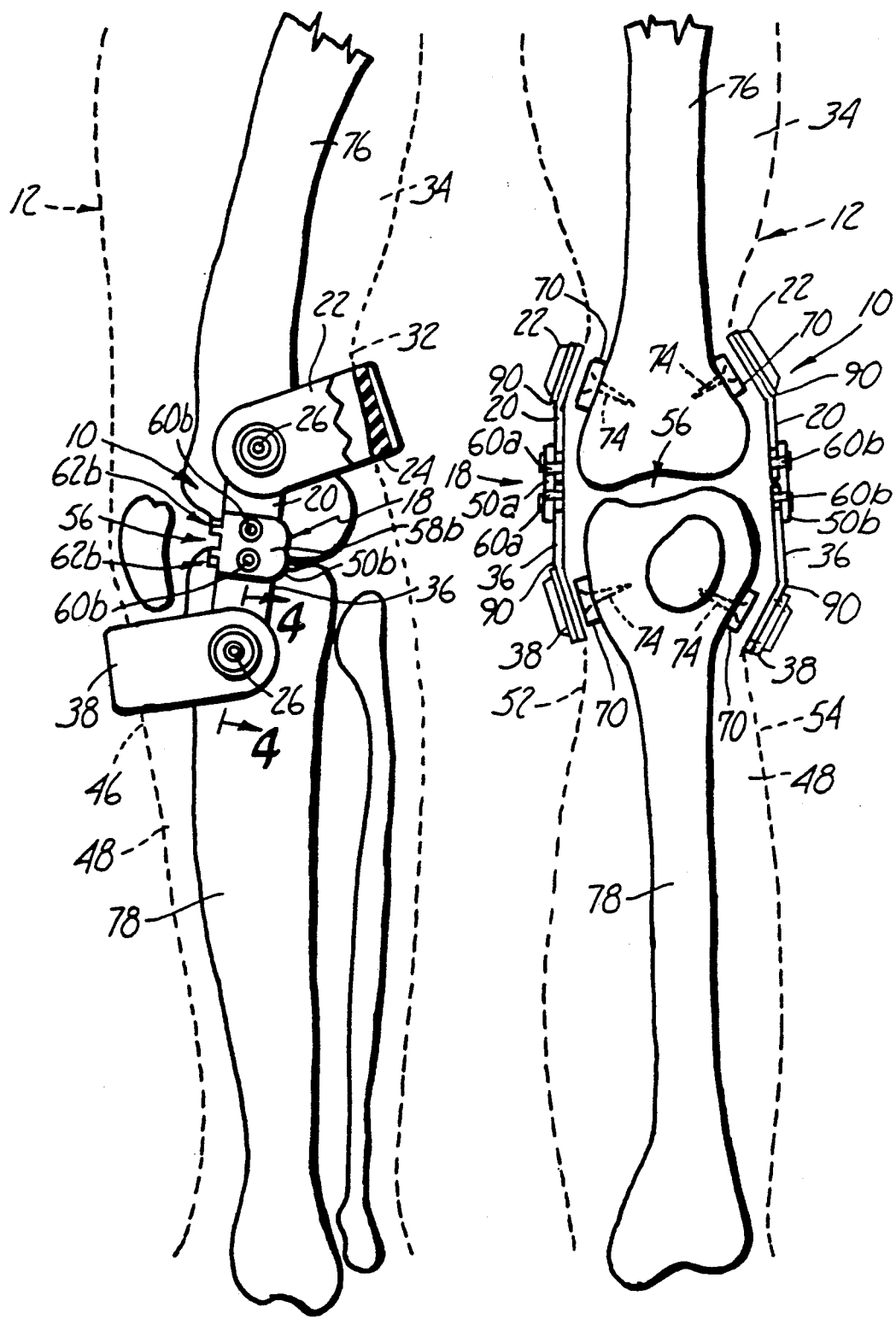
FIG. 1 is side elevational view partially in section of the knee brace of the present invention secured to the leg of a wearer.
FIG. 2 is a front elevational view of the knee brace shown in FIG. 1.

A knee brace 10 in accordance with the present invention is illustrated in FIGS. 1 and 2 as it would be secured to a leg 12 of a wearer. As perhaps shown most clearly in FIG. 3, knee brace 10 includes an upper support assembly 14 pivotally connected to a lower support assembly 16 by pivot mechanism 18.

Upper support assembly 14 includes a pair of substantially rigid upper support elements 20. A flexible band 22 extends between the upper support elements 20 and includes a padded member 24. A pair of fasteners 26 (only one of which is shown in FIG. 3) pivotally secure opposite ends 28 of the flexible band 22 to the first ends 30 of the upper support elements 20. As seen in FIG. the flexible band 22 is configured to engage a posterior portion 32 of a thigh 34. The fasteners 26 permit relative movement between the band 22 and the upper support elements 20 so that the flexible band 22 can conform to leg movement of a wearer.

As seen in FIG. 3, lower support assembly 16 is a mirror image of the upper support assembly 14 and includes a pair of substantially rigid lower support elements 36. A flexible band 38 extends between the lower support elements 36 and includes a padded member 40. Opposite ends 42 of the flexible band 38 are pivotally secured to first ends 44 of the lower support elements 36 by fasteners 26 (only one of which is shown in FIG. 3). As seen in FIG. 1, fasteners 26 allow flexible band 38 to conform to leg movement of a wearer by permitting relative movement between the flexible band 38 and lower support elements 36. The flexible band 38 is configured to engage an anterior portion 46 of a calf 48.

As seen in FIG. 2, pivot mechanism 18 includes a pair of polycentric hinge members 50a and 50b that are configured to be oriented on the medial and lateral sides 52 and 54, respectively, of a knee joint 56. Each one of the hinge members 50a and 50b pivotally connects one upper support element 20 to one lower support element 36. Hinge members 50a and 50b are mirror images of one another but have the same principal components. Hence, like components will be described with like numerals with the appropriate subscript.

As shown best in FIG. 3, hinge members 50a and 50b each include a hinge plate 58a and 58b, respectively. Pivot pins 60a and 60b pivotally connect second ends 59 and 61 of upper and lower support elements 20 and 36, respectively, to the hinge plates 58a and 58b. Stop members 62a and 62b limit the range of movement between the upper and lower support elements 20 and 36 and thereby restrict leg extension to less than 180°. Stop members 62a and 62b include L-shaped stop elements 64a and 64b integral with the hinge plates 58a and 58b and located adjacent to the pivot pins 60a and 60b, respectively. Stop extensions 66a and 66b are integral with the second ends 59 and 61, respectively, of the upper and lower support elements 20 and 36. Stop extensions 66a and 66b contact the stop elements 64a and 64b, respectively, when the upper and lower support elements 20 and 36 form a continuous line as shown in FIGS. 1 and 3, and thereby limit leg extension.

A magnetic assembly secures each of the upper and lower support assemblies 14 and 16 of the knee brace 10 to the leg 12 of a wearer. In the embodiment shown in FIG. 2, the magnetic assembly includes implanted magnets 70 implanted beneath the tissue 72 (see FIG. 4) of the leg 12. Bone screws 74 are used to secure the implanted magnets 70 to a femur 76 and a tibia 78 so that they are oriented on the medial and lateral sides 52 and 54 of the leg 12.

As shown in FIGS. 3 and 4, the inner sides of the first ends 30 and 44 of the upper and lower support elements 20 and 36, respectively, are formed with concave cavities 80. Each cavity 80 includes a bottom portion 82 and an angled, continuous side wall 84. The cavities 80 are shaped to receive exterior magnets 86 of the magnetic assembly. The exterior magnets 86 are secured in the cavities 80 by any conventional means such as adhesive or screws. The polarity of the implanted magnets 70 is opposite that of the exterior magnets 86. Therefore, aligned and adjacent pairs of magnets 70 and 86 form a mutual attraction and cooperate to secure the brace 10 to the leg 12 of a wearer. The exterior magnets 86 include recesses 88. The recesses 88 are shaped to receive to a certain extent the implanted magnets 70 to help orient the knee brace 10 in the proper position relative to the femur 76 and tibia 78 of the leg 12 of a wearer. As seen in FIG. 2, the substantially rigid upper and lower support elements 20 and 36 can be deformed (e.g., bent along dotted lines 90) to conform to the particular shape of the leg 12 of the individual wearer.

This knee brace is relatively uncomplicated. Since it is referenced mechanically to the femur and tibia it provides enhanced medial and lateral stability to the knee joint. In addition, since the brace is referenced mechanically from the bones in the leg and not merely secured to the flesh surrounding the knee joint, it mimics the support no longer provided by muscles and ligaments in the injured knee. Moreover, since this knee brace does not have large rigid, constricting cuffs with numerous straps, it provides better comfort and as a result causes fewer abrasions and pressure sores.

Although the present invention has been described with reference to preferred embodiments, workers skilled in the art will recognize that changes may be made in form and detail without departing from the spirit and scope of the invention.

What is claimed is:

1. An orthopedic appliance for a joint on a limb of a wearer, comprising:
    an upper support assembly configured to engage a limb on a first side of a joint;
    a lower support assembly configured to engage a limb on a second side of a joint;
    a pivot mechanism for pivotally connecting the upper support assembly to the lower support assembly; and
    a magnetic assembly for securing the upper and lower support assemblies to a limb of a wearer.

2. The orthopedic appliance of claim 1 wherein the upper support assembly includes:
    a first upper support element configured to be positioned adjacent to a medial side of a joint; and
    a second upper support element configured to be positioned adjacent to a lateral side of a joint.

3. The orthopedic appliance of claim 2 wherein the lower support assembly includes:
    a first lower support element configured to be positioned adjacent to a medial side of a joint; and
    a second lower support element configured to be positioned adjacent to a lateral side of a joint.

4. The orthopedic appliance of claim 3 wherein the pivot mechanism includes:
    a first hinge member pivotally connecting the first upper support element to the first lower support element; and
    a second hinge member pivotally connecting the second upper support element to the second lower support element.

5. The orthopedic appliance of claim 4 wherein each of the first and second hinge members is a polycentric hinge for limiting the range of movement between the upper and lower support elements.

6. The orthopedic appliance of claim 4 wherein the first and second hinge members each include:
    a hinge plate;

pivot member for pivotally connecting a respective upper support element to the hinge plate; and a second pivot member for pivotally connecting a respective lower support element to the hinge plate.

7. The orthopedic appliance of claim 6 wherein the hinge plates include stop elements and the support elements include stop extensions engageable with the stop elements to limit the range of movement between the upper and lower support elements.

8. The orthopedic appliance of claim 3 wherein the upper support assembly further includes an upper band extending between the first and second upper support elements and adapted to traverse a posterior portion of a limb on the first side of a joint.

9. The orthopedic appliance of claim 8 wherein the lower support assembly further includes a lower band extending between the first and second lower support elements and adapted to traverse an anterior portion of a limb on the second side of a joint.

10. The orthopedic appliance of claim 9 wherein the upper and lower bands are constructed of a flexible, padded material.

11. The orthopedic appliance of claim 1 wherein the magnetic assembly includes a magnet configured for mounting proximal to a joint beneath the tissue of a limb.

12. The orthopedic appliance of claim 1 wherein the magnetic assembly includes:
    a first magnetic member configured for mounting to a first bone on the first side of a joint beneath the tissue of a limb; and
    a second magnetic member configured for mounting to a second bone on the second side of a joint beneath the tissue of a limb, the first and second magnetic members magnetically securing the upper and lower support assemblies, respectively, to a limb of a wearer.

13. The orthopedic appliance of claim 12 wherein the magnetic assembly further includes:
    a third magnetic member mounted on the upper support assembly for cooperating with the first magnetic member; and
    a fourth magnetic member mounted on the lower support assembly for cooperating with the second magnetic member.

14. The orthopedic appliance of claim 3 wherein the magnetic assembly includes:
    a first pair of magnets, one being attached to each of a lateral side and a medial side of a first bone on the first side of a joint beneath the tissue of a limb; and
    a second pair of magnets, one being attached to each of a lateral side and a medial side of a second bone on the second side of a joint beneath the tissue of a limb.

15. The orthopedic appliance of claim 14 wherein the magnetic assembly further includes:
    a third pair of magnets, one being mounted to each of the first and second upper support elements for cooperating with the first pair of magnets; and
    a fourth pair of magnets, one being mounted to each of the first and second lower support elements for cooperating with the second pair of magnets to secure the orthopedic appliance to a limb of a wearer.

16. The orthopedic appliance of claim 15 wherein each of the magnets of the third and fourth pair of magnets include a recess for receiving a respective magnet of the first and second pair of magnets.

17. The orthopedic appliance of claim 15 wherein the first and second pairs of magnets are configured for attachment to a femur and tibia, respectively, of a leg of a wearer.

18. An orthopedic brace for bracing first and second bones connected by a joint, comprising:
    a first implantable magnetic member configured for mounting to a first bone on a first side of a joint;
    a second implantable magnetic member configured for mounting to a second bone on a second side of a joint; and
    a brace member including:
        a first support member;
        a second support member;
        a hinge coupling the first and second support members for concerted rotational movement with a joint about a pivot axis of a joint;
        a first exterior magnetic member mounted to a first support member and magnetically cooperable with the first implantable magnetic member to secure the first support member with respect to the first implantable magnetic member; and
        a second exterior magnetic member mounted to the second support member and magnetically cooperable with the second implantable magnetic member to secure the second support member to the second implantable magnetic member.

19. The orthopedic brace of claim 18, and further including:
    a third implantable magnetic member configured for mounting to a first bone on the first side of a joint;
    a fourth implantable magnetic member configured for mounting to a second bone on the second side of a joint; and
    the brace member further including:
        a third support member;
        a fourth support member;
        a hinge coupling the third and fourth support members for concerted rotational movement with a joint about the pivot axis of a joint;
        a third exterior magnetic member mounted to the third support member and magnetically cooperable with the third implantable magnetic member to secure the third support member with respect to the third implantable magnetic member; and
        a fourth exterior magnetic member mounted to the fourth support member and magnetically cooperable with the fourth implantable magnetic member to secure the fourth support member to the fourth implantable magnetic member.

20. The orthopedic brace of claim 19, and further including:
    a first flexible band secured between the first and third support members; and
    a second flexible band secured between the second and fourth support members.

21. The orthopedic brace of claim 18 wherein the first exterior magnetic member is a magnet and the second exterior magnetic member is a magnet.

22. The orthopedic brace of claim 18 wherein the first and second implantable magnetic members are first and second implantable polarized magnets, respectively.

23. The orthopedic brace of claim 22 wherein the first and second exterior magnetic members are first and second polarized exterior magnets, respectively, whose polarity is opposite the first and second polarized implantable magnets.

24. The orthopedic brace of claim 19 wherein the first, second, third and fourth exterior magnetic members are each a magnet.

25. The orthopedic brace of claim 19 wherein the first, second, third and fourth exterior magnetic members are first, second, third and fourth polarized exterior magnets, respectively.

26. The orthopedic brace of claim 25 wherein the first, second, third and fourth implantable magnetic members are first, second, third and fourth polarized implantable magnets, respectively, whose polarity is opposite that of the first, second, third and fourth polarized exterior magnets.

* * * * *

UNITED STATES PATENT AND TRADEMARK OFFICE
CERTIFICATE OF CORRECTION

PATENT NO. : 5,092,320

DATED : March 3, 1992

INVENTOR(S) : DONALD D. MAURER

It is certified that error appears in the above-identified patent and that said Letters Patent is hereby corrected as shown below:

Col. 5, line 1, before "pivot member", insert "a first"

Signed and Sealed this

Third Day of August, 1993

Attest:

MICHAEL K. KIRK

Attesting Officer     Acting Commissioner of Patents and Trademarks